United States Patent [19]
Saito et al.

[11] Patent Number: 5,573,646
[45] Date of Patent: Nov. 12, 1996

[54] ELECTROCHEMICAL FLUID DELIVERY DEVICE

[75] Inventors: Satoshi Saito; Yuko Fujita, both of Kyoto, Japan

[73] Assignee: Japan Storage Battery Co., Ltd., Kyoto, Japan

[21] Appl. No.: 502,361

[22] Filed: Jul. 14, 1995

[30] Foreign Application Priority Data

Jul. 14, 1994 [JP] Japan .................................. 6-194503

[51] Int. Cl.$^6$ .............................. C25B 9/00; C25B 11/03; C25B 13/04; C25B 15/08
[52] U.S. Cl. ......................... 204/266; 204/277; 204/283; 204/291
[58] Field of Search .................................. 204/277, 278, 204/265, 266, 284, 271, 283

[56] References Cited

U.S. PATENT DOCUMENTS

| | | | |
|---|---|---|---|
| 3,996,126 | 12/1976 | Rasmussen | 204/271 |
| 4,605,483 | 8/1986 | Michaelson | 204/277 X |
| 4,687,423 | 8/1987 | Maget et al. | 417/379 |
| 4,886,514 | 12/1989 | Maget | 604/891.1 |
| 4,902,278 | 2/1990 | Maget et al. | 604/132 |
| 5,186,805 | 2/1993 | Gross et al. | 204/266 X |
| 5,395,501 | 3/1995 | Rohrbacker et al. | 204/266 X |
| 5,423,454 | 6/1995 | Lippman | 204/271 X |
| 5,454,922 | 10/1995 | Joshi et al. | 204/265 |

FOREIGN PATENT DOCUMENTS

| | | |
|---|---|---|
| 58-48209 | 10/1983 | Japan . |
| 2302264 | 12/1990 | Japan . |

*Primary Examiner*—Donald R. Valentine
*Attorney, Agent, or Firm*—Sughrue, Mion, Zinn, Macpeak & Seas

[57] ABSTRACT

An electrochemical fluid delivery device according to the present invention includes an electrochemical cell and a flexible bladder having a first chamber for reservoiring a fluid and a second chamber into which gas generated by the electrochemical cell is introduced. The gas compresses the first chamber to deliver the fluid from a delivery port of the first chamber. The bladder is formed of three sheets that are stacked, and their edge portions are joined to each other so that first and second sheets form the first chamber as well as the second sheet and a third sheet form the second chamber. A fluid delivery port and a gas introduction port are provided in the first and second chambers, respectively. The fluid delivery port is also used as a fluid pour port. Alternatively, the fluid pour port is independently provided.

17 Claims, 3 Drawing Sheets

ELECTROCHEMICAL FLUID DELIVERY DEVICE

BACKGROUND OF THE INVENTION

1. Field of the Invention

The present invention relates to a fluid delivery device for accurately delivering fluid.

2. Description of the Related Art

Recently, various types of infusion pumps are used to inject liquid medicine into human body with accuracy.

The conventional infusion pumps are classified into 4 types that are a syringe pump, peristaltic (rotor type) pump, finger pump and bellows pump. Except for the bellows pump, each of the above infusion pumps is provided with a stepping motor, rotary solenoid motor or DC motor so that liquid medicine can be delivered by a drive force generated by the motor. Accordingly, since a complicated control mechanism is adopted to control an infuse volume of the liquid medicine, the weights and dimensions of these pumps are usually large and further their cost is expensive. Therefore, it is common that these pumps are used beside the bed in a hospital, and are not suitable for portable or disposable use. In the bellows pump, vaporization pressure of freon gas is utilized, and liquid medicine is delivered by the action of vaporization pressure. However, it is difficult to control the vaporization pressure of freon gas. Especially, when a very small amount of liquid medicine is injected over a long period of time, the accuracy of injection is difficult to maintain.

One of the present inventors made an application for a patent of the apparatus having a pumping function where the rate of gas flow is controlled with an electrochemical cell in which gas is generated when a direct current is made to flow (Japanese Patent No. 1214001). Recently, an electrochemically driven drug dispenser has been proposed, in which the aforementioned principle is adopted. In this system, liquid medicine is delivered by the action of gas generated in proportion to a quantity of electricity when a direct current is made to flow in the electrochemical cell part. According to the invention proposed by H. J. R. Maget disclosed in U.S. Pat. Nos. 4,687,423, 4,886,514 and 4,902,278, the electrochemical cell is composed of a polymer electrolyte membrane and a pair of electrodes attached onto both sides of the electrolyte membrane. In this cell, when a current is allowed to flow between both electrodes so that an electrochemical active mass is supplied to a first electrode, the electrochemical active mass is ionized there, and the generated ions move through the electrolyte membrane and arrive at a second electrode. At the second electrode, ions are converted into a pressurized gas, which is used as a drive source for pushing the diaphragm. When hydrogen is used as the electrochemical active mass, hydrogen functions as the pressurized gas. On the other hand, when oxygen and air are used as the electrochemical active mass, oxygen functions as the pressurized gas.

However, in the drug dispenser disclosed in U.S. Pat. No. 4,687,423, gas is pressurized by the electrochemical cell and is released through a pump valve, when its pressure is increased to a predetermined value. By the action of this gas pressure, a flexible diaphragm is subjected to pulsation so that the liquid medicine in a pump chamber is delivered. When this drug dispenser is operated, a current is made to flow in a predetermined direction, however, it is necessary to accurately adjust a relationship between the pressure required for expanding and contracting the flexible diaphragm including a part of the wall of the pump chamber and the pressure required for operating a pump valve of the pressure release mechanism. Further, the electrochemical cell, pump chamber and pressure release mechanism are integrated into one unit. Therefore, when different types of medicine are used, the pump chamber have to be washed each time. Moreover, the structure of the apparatus is considerably complicated. As a result, the cost of the apparatus is very high. Therefore, it is impossible to put the pump into practical use.

In the drug dispenser described in U.S. Pat. No. 4,886,514, the electrochemical pump and liquid medicine container are integrated into one unit. In this case, the flexible diaphragm, bellows or sliding wall, provided for separating the electrochemical pump from the liquid medicine container, is deformed or moved so that the medicine in the medicine container can be delivered. In the drug dispenser, the electrochemical pump and the medicine container are integrated into one unit, and can not be separated from each other. Accordingly, it is difficult to put this apparatus in practical use. Furthermore, this apparatus also has some inconvenience such as the medicine container having to be washed each time when different types of liquid medicines are used.

In the fluid delivery pump described in U.S. Pat. No. 4,902,278, a prime mover portion, in which the power supply part and the electrochemical cell part are integrated into one unit, can be separated from the fluid reservoir part. The flexible membrane of the fluid reservoir part is pushed by the gas generated from the prime mover so that the fluid can be delivered. However, the structure of the fluid reservoir part of this apparatus is complicated. Therefore, the fluid reservoir part is not suitable for disposable use. Further, it is complicated to put liquid medicine into the fluid reservoir part.

For a remodeled pump of this electrochemical liquid transporting pump, a method using electrolysis of water is provided (Unexamined Japanese Patent Publication No. Hei. 2-302264). According to this method, an electrochemical cell is used in which a cathode is integrally joined on one side of an ion exchange membrane and an anode is integrally joined on the other side of the ion exchange membrane. Alternatively, an electrochemical cell is used in which a cathode and an anode are integrally joined on one side of an ion exchange membrane under the condition that the cathode and the anode are separated from each other so that they can be insulated. Water is contained in the above electrochemical cell, and a direct current is made to flow in both electrodes so that hydrogen and oxygen are generated by the electrolysis of water. Generated hydrogen or oxygen, or alternatively a mixture gas of hydrogen and oxygen is used for the pressure source of the infusion pump.

Moreover, when the liquid medicine is delivered by the electrochemically driven drug dispenser, there is a method in which the liquid medicine is aspirated between the outer tube and the suction member of a syringe and the suction member is pushed by the pressure of gas generated by the electrochemical cell. However, since the friction resistance between the outer tube and a piston made of rubber provided at the top end of the suction member disperses, it has an inconvenience in that the current value of the electrochemical cell is individually set so as to correspond to each used syringe. In addition, since the outer tube or the suction member has a taper, the friction resistance is different due to the position of the suction member. Therefore, it is often observed that the delivery speeds of the medicine liquid at the initial period and the end period during an injection are different from each other.

SUMMARY OF THE INVENTION

The present invention has been accomplished to solve the above problems of the conventional electrochemical infusion pump. Accordingly, it is an object of the present invention to provide a simple, small, portable, disposable and inexpensive electrochemical fluid delivery device easily operated in practical use.

The electrochemical fluid delivery device according to the present invention is comprised of an electrochemical cell for generating gas when direct current is applied; a bladder including a first chamber for reservoiring fluid therein and a second chamber to which the gas generated by the electrochemical cell is introduced, a periphery or peripheral wall portion of the bladder and a partition between the first and the second chambers being formed of flexible sheet material; and a fluid delivery port provided in the first chamber, the fluid in the first chamber compressed by a pressure of the gas introduced into the second chamber being delivered.

The fluid delivery device according to the present invention is suitable for delivering the liquid medicine to a patient, and further, it can be applied to various kinds of the delivery of liquids and gases for industrial use or the like.

BRIEF DESCRIPTION OF THE DRAWINGS

In the accompanying drawings.

DETAILED DESCRIPTION OF THE INVENTION

Figure 1A:
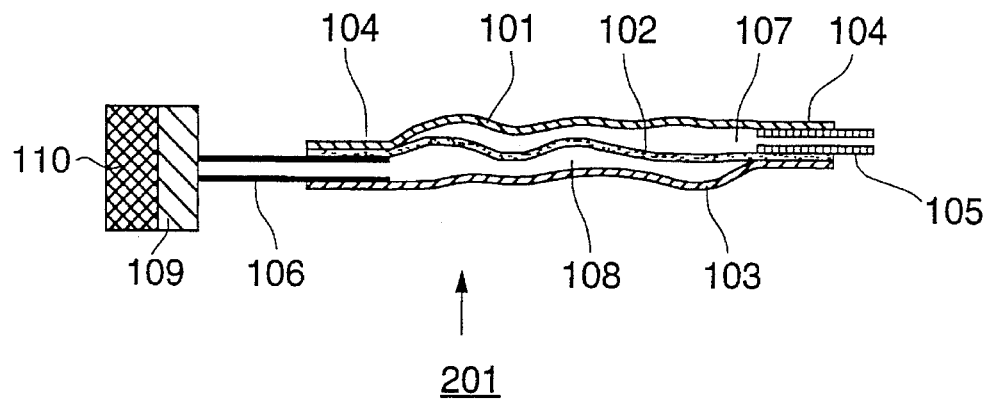
FIG. 1A is a sectional view showing an electrochemical fluid delivery device of a first embodiment in a state where it is not used.

The detailed description of the present invention will be described as follows referring to the accompanying drawings.

An electrochemical fluid delivery device of the present invention includes an electrochemical cell and a flexible bladder having a first chamber and a second chamber, wherein gas generated by the electrochemical cell is introduced into the second chamber to compress the first chamber so that a fluid is pushed out from the delivery port thereof.

The feature of the electrochemical fluid delivery device according to the present invention is that a fluid reservoir and a compressing portion for compressing the gas generated by the electrochemical cell are formed by the flexible bladder. Such a flexible bladder can be easily formed by the following manner. Three flexible sheets are stacked, and their edge portions are joined to each other by a method of an adhesive, heat sealing, stitching or the like. Consequently, the first sheet chamber is formed between a first and a second sheet, and the second chamber is formed between the second sheet and a third sheet.

Incidentally, the bladder having two chambers is produced by the following manner. Three sheets are joined to each other while a tube-shaped fluid pour port and fluid delivery portion are provided between the edge portions of two sheets forming the first chamber, and a tube-shaped introducing port of the gas generated by the electrochemical cell is provided between the edge portions of two sheets forming the second chamber. Two tubes may be provided at the first chamber, one as the fluid pour port and the second as the fluid delivery port. Alternatively, one tube may be provided as both the fluid pour port and the fluid delivery port.

The sheet material of the bladder is polyvinyl chloride, polyethylene, polypropylene or the like. Especially, an organic polymer capable of being joined by the heat sealing, stitching or the like is preferable. However, the material is not limited into such polymer. According to Circumstances, a thin metallic sheet can be used. Further, when selecting the material, it is necessary to consider that the material gives no bad influence even if it contacts with the fluid, and it has a small permeation of oxygen and hydrogen generated by the electrochemical cell. Moreover, the materials of the respective above described three sheets may be the same or different from each other.

It is assumed that the fluid delivery device according to the present invention is used in the atmosphere under the pressure of P. The gas generated by the electrochemical cell is filled within the second chamber formed by the second and third sheets so that the pressure in the chamber becomes P' slightly larger than P. Accordingly, the second and the third sheets forming the second chamber are subjected to expand because they are pressurized from the inside. On the other hand, since the fluid delivery port provided at the first chamber opens to the outside, the constant pressure of P is given to the fluid in the first chamber. Therefore, while the pressure of P' slightly lager than P is given to the inside of the first chamber from the second chamber side, the fluid in the first chamber is delivered to the outside from the fluid delivery port. Accordingly, even if the generation of the gas from the electrochemical cell is continued, the pressure in the second chamber is maintained in the pressure of P so that the first chamber is successively contracted to deliver the fluid in the first chamber to the outside. In addition, it is possible to provide a check valve in the fluid delivery port so as to prevent the backflow of the fluid.

Incidentally, the electrochemical cell may be provided to be separated from the bladder so that, for example, the gas generated by the electrochemical cell is introduced into the second chamber through a tube. Alternatively, the electrochemical cell may be directly mounted onto the third sheet of the bladder by a method of joining or the like.

The amount of the gas generated by the electrochemical cell is theoretically 420 ml (0° C., 1 atom) for hydrogen and 210 ml (0° C., 1 atom) for oxygen with respect to the quantity of electricity of 1 Ah. Due to the permeation of the gas, the recombination reaction of the oxygen and hydrogen occurs on the surface of the electrodes or the like. The actual gas amount is 70–95% of the theoretical amount which depends on the operating current density. In addition, the necessary size of the electrochemical cell depends on, for example, the set delivery speed of the liquid medicine and the total liquid medicine delivery amount.

Although the direct current is needed to operate the electrochemical cell, the direct current converted from the alternating current power supply can be supplied to the electrochemical cell when it is used at the bed side and the comparatively large amount of liquid medicine is necessary to supply. Additionally, when the comparatively small amount of liquid medicine is to be supplied, for example, 50 ml of liquid medicine is supplied in one day, a small battery can be employed as the power source. In case of using such a small battery, the battery and the electrochemical cell is directly mounted on the edge portion of the bladder so that the fluid delivery device would become a portable one. If it is used for medical treatment, a patient freely conducts the injection her/himself.

Moreover, in the fluid delivery device according to the present invention, the desirable delivery amount of the fluid is determined by the gas generated by the electrochemical cell. The volume of the gas generated by the electrochemical cell is set in accordance with the quantity of electricity thereof, that is, (current×time). Accordingly, the delivery amount of the fluid per an unit time is determined by the value of the current. Alternatively, if a constant current flows, the total delivery amount of the fluid is determined by time. Therefore, as described above, the fluid can be precisely delivered by the extremely simple method.

A first embodiment of the electrochemical fluid delivery device according to the present invention will be described as follows referring to the accompanying drawings.

Figure 2:
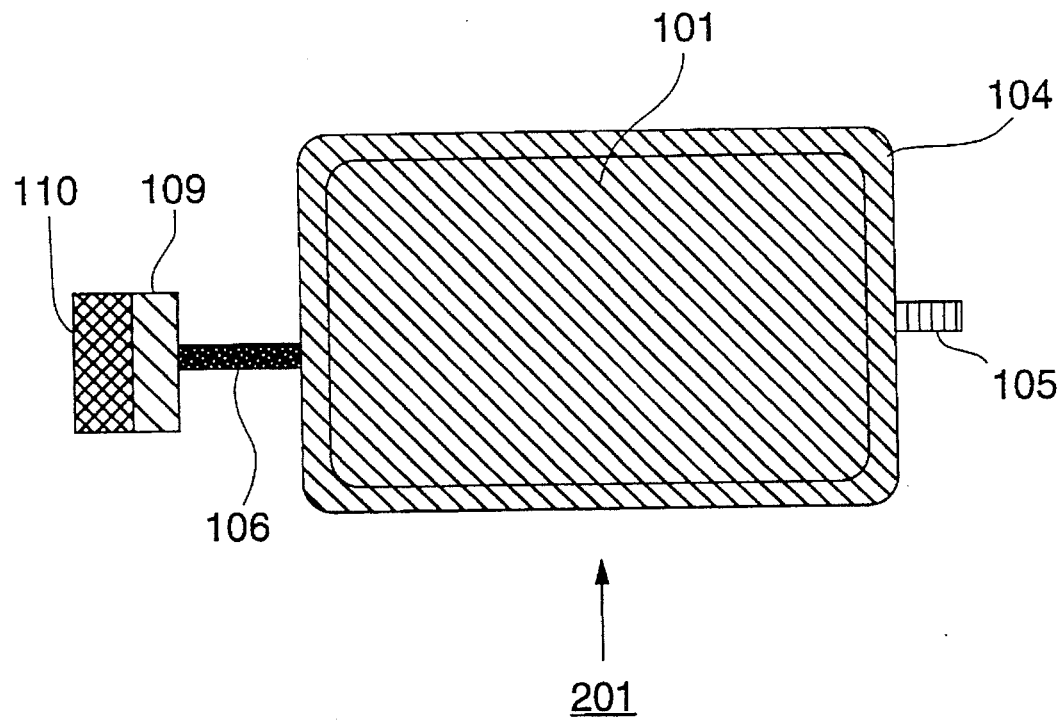
FIG. 2 is a plan view showing the electrochemical fluid delivery device of the first embodiment.

FIG. 2 is a plan view showing the electrochemical fluid delivery device 201 of the first embodiment in a state where it is not used. In the drawing, reference numeral 101 represents a first sheet. Although second and third sheets 102 and 103 are not indicated in FIG. 2, they are arranged at the rear of the first sheet 101. These sheets are made of polyvinyl chloride, and have a size of 150 mm×100 mm. Reference numeral 104 represents an integrated edge portion in which respective edge portions of three sheets are integrated to be sealed by stitching. Reference numerals 105 and 106 represent a fluid delivery port and a gas introduction tube, respectively. They are made of polyvinyl chloride, and have an outer diameter of 6 mm and an inner diameter of 4 mm. Reference numeral 109 represents a water electrolysis cell as an electrochemical cell in which two porous platinum electrodes as an anode and cathode having a diameter of 8 mm are joined on both sides of a solid polymer protonic conductor as a solid electrolyte having a diameter of 12 mm by electroless plating method. Reference numeral 110 is a power supply which is a combination of a battery and a constant-current supply.

The fluid delivery device is produced in the following manner. Three polyvinyl chloride sheets are stacked on each other. A tube 105 made of polyvinyl chloride as the fluid delivery port is put between the first and the second sheets 101 and 102. The other tube made of polyvinyl chloride as the gas introduction tube 106 is put between the second and the third sheets 102 and 103. Thereafter, the edge portions of the sheets are joined by stitching.

Figure 1B:
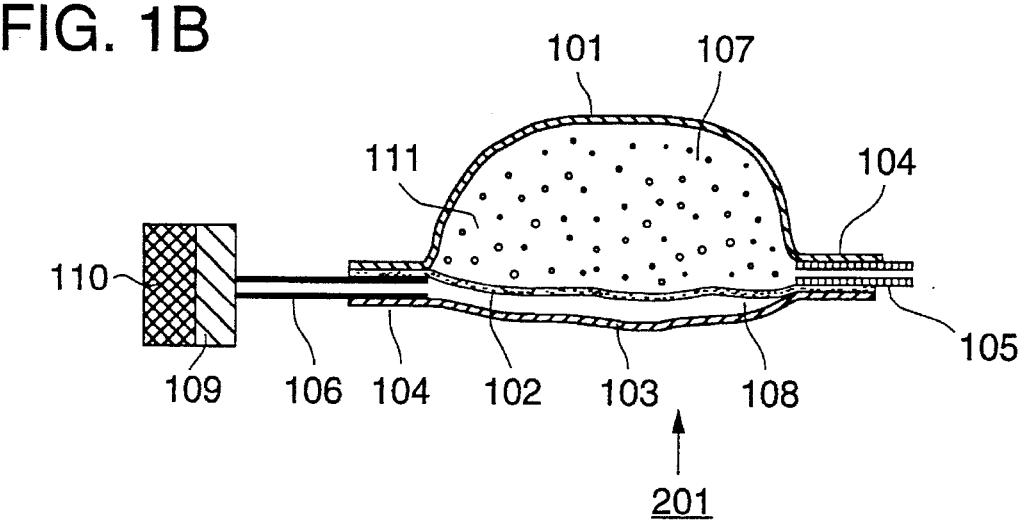
FIG. 1B is a sectional view showing the electrochemical fluid delivery device of the first embodiment in a state where it is immediately before being used.
Figure 1C:
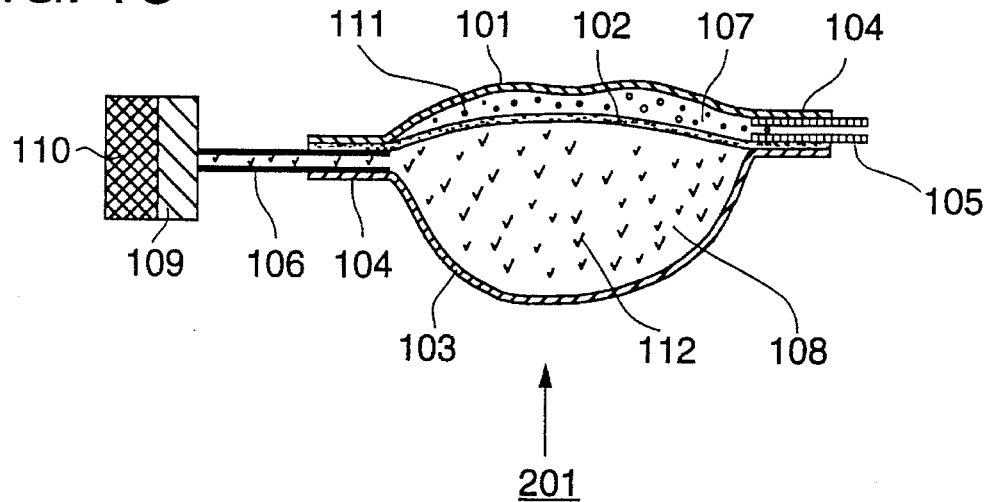
FIG. 1C is a sectional view showing the electrochemical fluid delivery device of the first embodiment in a state where it is immediately before being finished.

Further, FIG. 1A is a sectional view showing an electrochemical fluid delivery device of the first embodiment in a state where it is not used. FIG. 1B is a sectional view showing the electrochemical fluid delivery device of the first embodiment in a state where it is immediately before being used. FIG. 1C is a sectional view showing the electrochemical fluid delivery device of the first embodiment in a state where it is immediately before being finished.

In the drawings, the explanations on the similar components as in FIG. 2 are omitted here. Reference numeral 107, which represents a first chamber formed by the first and the second sheets 101 and 102, acts as a fluid reservoir. Reference numeral 108, which represents a second chamber formed by the second and the third sheets 102 and 103, acts as a compressing portion. That is, the second sheet 102 is a partition between the first chamber 107 and the second chamber 108. Reference numerals 111 and 112 represent a physiological salt solution as a fluid and compressing gas, respectively.

FIG. 1A shows an unused state of the fluid delivery device 201 in which the small amount of air exists in the first and a second chambers 107 and 108 having small volumes.

FIG. 1B shows a state where the fluid delivery device 201 is immediately before being used, in which the first chamber 107 is filled with the physiological salt solution and the volume of the second chamber is small. Next, if the direct current of 50 mA flows from the power supply 110 to the electrochemical cell 109, the electrolytic analysis reaction of water is caused in the electrochemical cell 109, and oxygen generated from the anode thereof is introduced from the gas introduce tube 106 to the second chamber 108. The application of the current is maintained so as to increase the pressure of oxygen in the second chamber 108. If the pressure of the atmosphere is 1 atm. and the inner pressure of the second chamber 108 becomes slightly larger than 1 atm., the physiological salt solution 111 is delivered at a rate of 10 ml per one hour for ten hours.

FIG. 1C shows a state where the fluid delivery device 201 is immediately before being finished, in which the first chamber 107 is contracted, the small amount of the physiological salt solution 111 remains therein, and on the other hand, the second chamber 108 is filled with oxygen gas 112.

Incidentally, if hydrogen generated by the cathode is introduced into the second chamber 208, the current value is 25 mA. Whereas, if oxygen and hydrogen generated by both electrodes are used, the current value is 17 mA.

Now, referring to FIG. 3, a second embodiment of the present invention will be described as follows.

Figure 3:
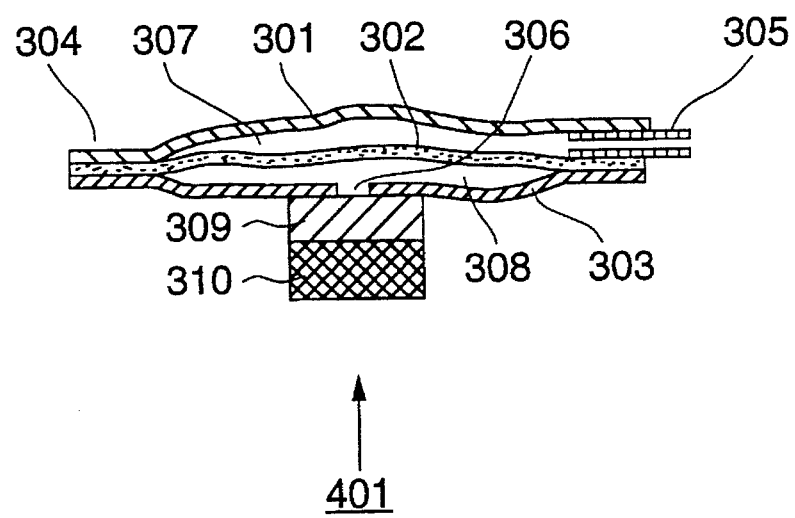
FIG. 3 is a sectional view showing an electrochemical fluid delivery device of a second embodiment.

FIG. 3 shows an electrochemical fluid delivery device 401 of the second embodiment in a state where it is not used, in which an electrochemical cell is directly mounted on a third sheet, that is, the electrochemical cell is integrally mounted on a second chamber. In the drawings, reference numerals 301, 302 and 303 represent a first sheet, a second sheet and a third sheet, respectively, which are made of polyvinyl chloride. Reference numeral 304 represents an integrated edge portion in which edge portions of three sheets are integrally joined by stitching. Reference numerals 305 and 306 represent a fluid delivery port and a gas introduction port provided in the third sheet 303. A first chamber 307 acting as a fluid reservoir is formed of the first and the second sheet 301 and 302. A second chamber 308 acting as a compressing portion is formed of the second and the third sheet 302 and 303. An electrochemical cell 309 is directly mounted on the outer surface of the second chamber 308, where a gas introduction tube is not needed. A power source 310 is a combination of a battery and a constant-current supply. The material and the size of each component is the same as that of the first embodiment. In addition, the electrochemical cell and the battery are also the same as those of the first embodiment.

In the electrochemical fluid delivery device, when the same current as that of the first embodiment is applied, the physiological salt solution is delivered at the same speed as in the first embodiment.

Figure 4:
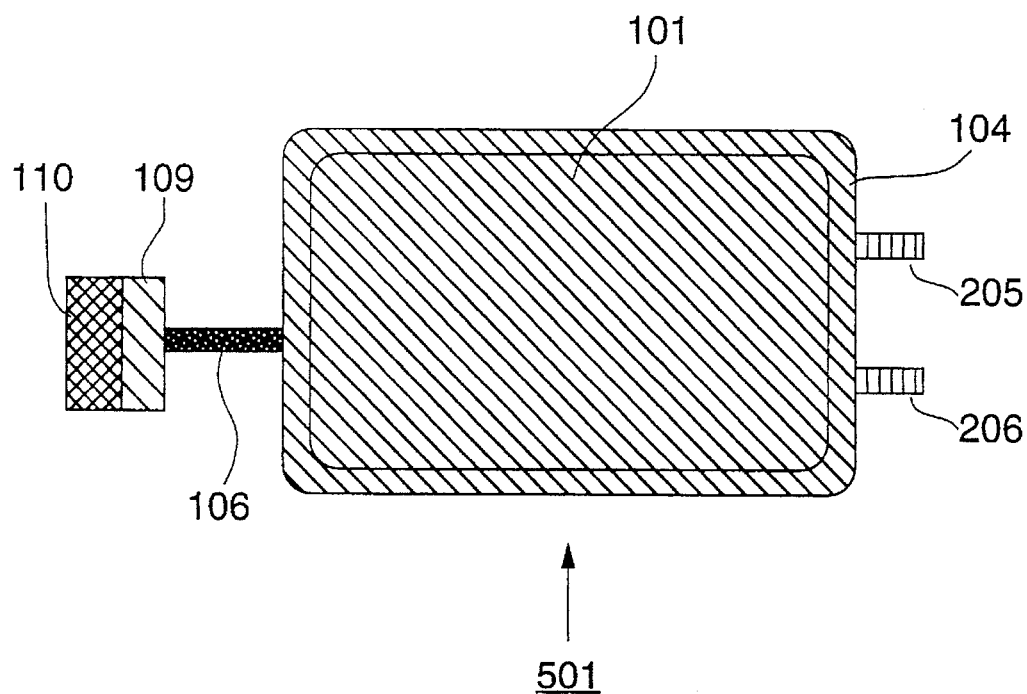
FIG. 4 is a plan view showing an electrochemical fluid delivery device of a third embodiment.

Next, referring to FIG. 4, a third embodiment of the present invention will be described. FIG. 4 is a plan view showing an electrochemical fluid delivery device 501 of the third embodiment. In the electrochemical fluid delivery device 501 of the third embodiment, components are the same as those of the first embodiment except providing a first tube 205 for a fluid pour port and a second tube 206 for a fluid delivery port in place of the tube 105 in the first embodiment.

Also, in this embodiment, when the same current as that of the first embodiment is applied, the physiological salt solution is delivered at the same speed as in the first embodiment.

Figure 5:
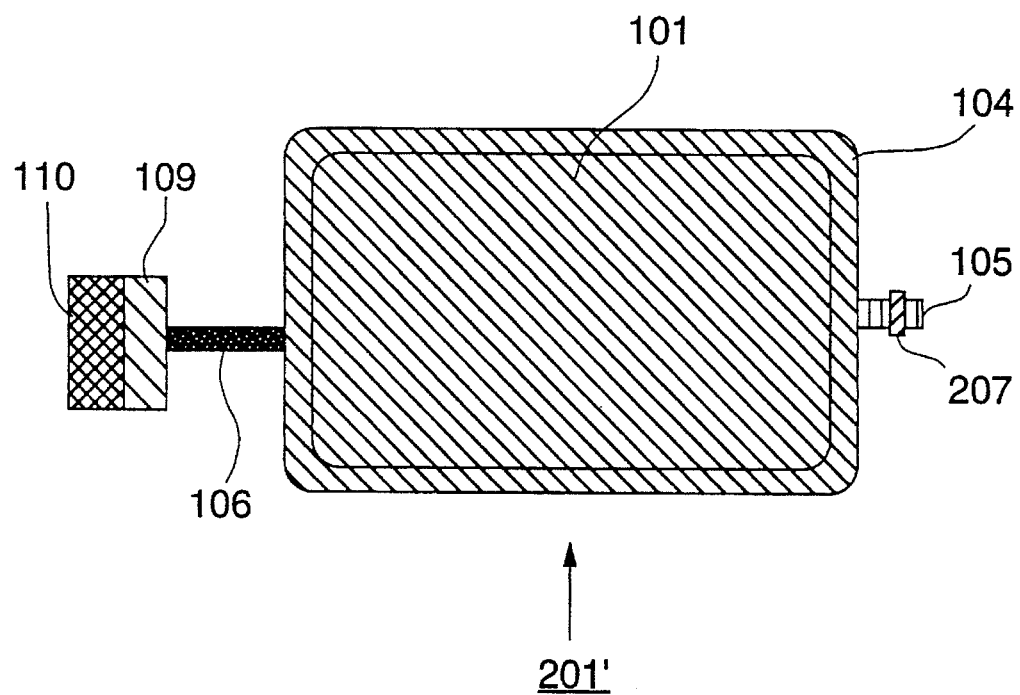
FIG. 5 is a plan view showing an electrochemical fluid delivery device of a fourth embodiment.

Further, referring to FIG. 5, a fourth embodiment of the present invention will be described. FIG. 5 is a plan view showing an electrochemical fluid delivery device 201' of the fourth embodiment. In the electrochemical fluid delivery device 201' of the fourth embodiment, components are the same as those of the first embodiment except providing a check valve 207 is provided in the tube 105. When this device is in an unused state, even if the fluid exists in the first chamber 107, the fluid can not leak back from the tube 105. Further, even when the pressure of the outside of this device is decreased during the operation of the device, the delivery of the fluid can be stopped by the check valve 207. Therefore, due to providing the check valve 207, it is possible to use gas as the fluid in place of liquid in this electrochemical fluid delivery device of the present invention.

Generally, all kinds of electrochemical cells which generate gas in proportion to the quantity of electricity while direct current is applied are used in the present invention. Specifically, the following cells can be used.

1) In the electrochemical cell, two porous metal electrodes as an anode and a cathode are joined to both side of a solid polymer cation exchange membrane, and both electrodes are in contact with water. Then, oxygen gas generated from the anode by applying a current or hydrogen gas generated from the cathode by applying a current or a mixture of these gases, is used.

2) In the electrochemical cell, two porous metal electrodes as an anode and a cathode are joined to both side of a solid polymer cation exchange membrane. The anode and the cathode are contacted with water and air or oxygen, respectively. Then, oxygen gas generated from the anode by applying a current is used.

3) In the electrochemical cell, a porous metal electrodes as an anode is joined to one side of a solid polymer cation exchange membrane, and manganese(IV) oxide as a cathode is joined to the other side thereof. Then, oxygen gas generated from the anode by applying a current is used.

4) In the electrochemical cell, a porous metal electrode as an anode is joined to one side of a solid polymer anion exchange membrane, and nickel(II) hydroxide or manganese(IV) oxide as an cathode is joined to the other side thereof. Then, oxygen gas generated from the anode by applying a current is used.

5) In the electrochemical cell, one of various kinds of inorganic protonic conductors, for example, dodeca molybdophosphoric acid ($H_3PMo_{12}O_{40} \cdot 29H_2O$), hydrogen uranyl phosphate ($HUO_2PO_4 \cdot 4H_2O$), hydrous antimony (V) oxide ($Sb_2O_5 \cdot H_2O$) or the like is used as an electrolyte to electrolyze water. Then, oxygen gas or hydrogen gas or a mixture of these gases generated during the electrolysis, is used.

The electrochemical fluid delivery device of the present invention is produced in the following extremely simple manner. Three flexible sheets are stacked, and the tube or tubes as the fluid pour port, the fluid delivery port and the gas introduce port are put between two adjacent sheets. The edge portions of the sheets are integrally joined. Therefore, the fluid delivery device of the present invention has a simple structure and optional size, thereby being produced at low cost. Further, the fluid delivery device according to the present invention includes three flexible sheets forming bladder having two chambers, the electrochemical cell and power source. The device except the electrochemical cell and power source can be deformed for portable use in various kinds of shapes. Accordingly, the device of the present invention is very useful because it is a portable device which is carried in a pocket of a cloth or the like.

Further, the fluid delivery device according to the present invention can be miniaturized by its weight, and its operation thereof is very easy. Especially, when the device of the present invention is used for the liquid medicine delivery in the medical treatment, it is very useful for a patient.

As described above, the fluid delivery device according to the present invention has a simple structure, can be produced at low cost, and is simple to treat. Accordingly, the device of the present invention can overcome the disadvantages in the conventional fluid delivery device using a bellows pump, diaphragm pump, electrochemical liquid delivery pump or the like. Accordingly, the industrial worth of the delivery device according to the present invention is very excellent.

What is claimed is:

1. An electrochemical fluid delivery device comprising:
    an electrochemical cell part for generating gas when direct current is applied;
    a flexible bladder including a flexible peripheral wall portion and a flexible partition disposed within said flexible peripheral wall portion and which divides said flexible bladder into a first chamber for reservoiring fluid therein and a second chamber to which the gas generated by said electrochemical cell part is introduced, said flexible peripheral wall portion of said flexible bladder and said flexible partition between said first and second chambers being formed of flexible sheet material; and
    a fluid delivery port provided in said first chamber, wherein the fluid in said first chamber which is compressed by a pressure of the gas introduced into said second chamber, is delivered through said fluid delivery port.

2. An electrochemical fluid delivery device according to claim 1, wherein the gas generated by said electrochemical cell part is at least one of oxygen gas, hydrogen gas and a mixture of oxygen gas and hydrogen gas.

3. An electrochemical fluid delivery device according to claim 2, further comprising a tube provided between said electrochemical cell part and said second chamber, wherein the gas generated by said electrochemical cell part is introduced to said second chamber through said tube.

4. An electrochemical fluid delivery device according to claim 2, wherein said electrochemical cell part is integrally mounted on said second chamber.

5. An electrochemical fluid delivery device according to claim 1, further comprising a tube provided between said electrochemical cell part and said second chamber, wherein the gas generated by said electrochemical cell part is introduced to said second chamber through said tube.

6. An electrochemical fluid delivery device according to claim 1, wherein said electrochemical cell part is integrally mounted on said second chamber.

7. An electrochemical fluid delivery device according to claim 1, wherein said fluid delivery port is operative for pouring the fluid into said first chamber.

8. An electrochemical fluid delivery device according to claim 1, further comprising a fluid pour port provided in said first chamber, through which the fluid is poured into said first chamber.

9. An electrochemical fluid delivery device according to claim 1, wherein said bladder comprises a flexible first sheet and a flexible third sheet as said periphery thereof; a flexible second sheet as said partition thereof; a first tube for at least one of pouring and delivering the fluid, said first tube being provided between edge portions of said first and second sheets; and a second tube for introducing the gas generated by said electrochemical cell part, said second tube being provided between edge portions of said second and third sheets, edge portions of said first, second and third sheets being integrated to be sealed.

10. Art electrochemical fluid delivery device according to claim 9, wherein said bladder further comprises a third tube for only pouring the fluid, and said first tube is used for only delivering the fluid.

11. Art electrochemical fluid delivery device according to claim 1, wherein said bladder comprises a first flexible sheet and a third flexible sheet as said periphery thereof; a second flexible sheet as said partition thereof; a tube for pouring and delivering the fluid, said first tube being provided between edge portions of said first and second sheets; and a gas introduction port provided in said third sheet for introducing the gas generated by said electrochemical cell part into said second chamber;

further wherein said electrochemical cell part is integrally mounted on said second chamber.

12. An electrochemical fluid delivery device according to claim 1, wherein said electrochemical cell part includes an anode and cathode each comprising a porous metal electrode; and a solid polymer cation exchange membrane, said anode and cathode being joined on one side and the other side of said solid polymer cation exchange membrane, respectively, and operative to contact water;

further wherein at least one of oxygen and hydrogen gas generated from at least one of said anode and cathode is introduced into said second chamber.

13. An electrochemical fluid delivery device according to claim 1, wherein said electrochemical cell part includes an anode and cathode each comprising a porous metal electrode; and a solid polymer cation exchange membrane, said anode and cathode being joined on one side and the other side of said solid polymer cation exchange membrane, respectively, said anode operative to contact water and said cathode operative to contact at least one of air and oxygen;

further wherein oxygen gas generated by said anode is introduced into said second chamber.

14. An electrochemical fluid delivery device according to claim 1, wherein said electrochemical cell part includes an anode comprising a porous metal electrode; a cathode comprising manganese(IV) oxide; and a solid polymer cation exchange membrane, said anode and cathode being joined on one side and the other side of said solid polymer cation exchange membrane, respectively,;

further wherein oxygen gas generated by said anode is introduced into said second chamber.

15. An electrochemical fluid delivery device according to claim 1, wherein said electrochemical cell part includes an anode comprising a porous metal electrode; a cathode comprising at least one of nickel(II) hydroxide and manganese(IV) oxide; and a solid polymer anion exchange membrane; said anode and cathode being joined on one side and the other side of said polymer anion exchange membrane, respectively;

further wherein oxygen gas generated by said anode is introduced into said second chamber.

16. An electrochemical fluid delivery device according to claim 1, wherein said electrochemical cell part includes at least one inorganic protonic conductor to electrolyze water, and at least one of oxygen gas, hydrogen gas and the mixture of oxygen and hydrogen gases generated during the electrolysis is introduced into said second chamber.

17. An electrochemical fluid delivery device according to claim 16, wherein said inorganic protonic conductor is comprised of at least one of dodeca molybdophosphoric acid ($H_3PMo_{12}O_{40} \cdot 29H_2O$), hydrogen uranyl phosphate ($HUO_2PO_4 \cdot 4H_2O$), hydrous antimony (V) oxide ($Sb_2O_5 \cdot H_2O$).

* * * * *